(12) United States Patent
Aihara et al.

(10) Patent No.: US 10,431,341 B2
(45) Date of Patent: Oct. 1, 2019

(54) DETECTION DEVICE, METHOD, AND PROGRAM FOR ASSISTING NETWORK ENTROPY-BASED DETECTION OF PRECURSOR TO STATE TRANSITION OF BIOLOGICAL OBJECT

(71) Applicant: Japan Science and Technology Agency, Kawaguchi-shi (JP)

(72) Inventors: Kazuyuki Aihara, Tokyo (JP); Luonan Chen, Kobe (JP); Rui Liu, Guangzhou (CN)

(73) Assignee: Japan Science and Technology Agency, Kawaguchi-shi (JP)

( * ) Notice: Subject to any disclaimer, the term of this patent is extended or adjusted under 35 U.S.C. 154(b) by 178 days.

(21) Appl. No.: 14/437,650

(22) PCT Filed: Oct. 15, 2013

(86) PCT No.: PCT/JP2013/077929
§ 371 (c)(1),
(2) Date: Apr. 22, 2015

(87) PCT Pub. No.: WO2014/065155
PCT Pub. Date: May 1, 2014

(65) Prior Publication Data
US 2015/0302165 A1    Oct. 22, 2015

(30) Foreign Application Priority Data
Oct. 23, 2012 (JP) .................................. 2012-233886

(51) Int. Cl.
G01N 33/48   (2006.01)
G01N 33/50   (2006.01)
G16H 50/30   (2018.01)
G16B 5/00    (2019.01)
A61B 5/00    (2006.01)
G06Q 50/24   (2012.01)

(52) U.S. Cl.
CPC ........... *G16H 50/30* (2018.01); *A61B 5/7264* (2013.01); *G06Q 50/24* (2013.01); *G16B 5/00* (2019.02)

(58) Field of Classification Search
None
See application file for complete search history.

(56) References Cited

PUBLICATIONS

Espanol et al. Statistical mechanics of dissipative particle dynamics. Europhysics Letters, vol. 30, pp. 191-196. (Year: 1995).*

(Continued)

*Primary Examiner* — Russell S Negin
(74) *Attorney, Agent, or Firm* — Locke Lord LLP

(57) ABSTRACT

The invention provides a detection device, method, and program capable of highly accurately detecting a pre-disease state that indicates a precursor to a state transition from a healthy state to a disease state. The following processes are carried out: a process of obtaining measured data on genes, proteins, etc. related to a biological object as high-throughput data (s1), a process of selecting differential biological molecules (s2), a process of calculating the SNE of a local network (s3), a process of selecting a biomarker candidate (s4), a process of calculating an average SNE across the entire network (s5), and a process of determining and detecting whether or not the system is in a pre-disease state (s6).

10 Claims, 9 Drawing Sheets

(56) References Cited

PUBLICATIONS

J. G. Venegas et al., "Self-organized patchiness in asthma as a prelude to catastrophic shifts," Nature vol. 434, Apr. 7, 2005, pp. 777-782.
P.E. McSharry et al., "Prediction of epileptic seizures: are nonlinear methods relevant?," Nature Medicine, vol. 9, No. 3, Mar. 2003, pp. 241-245.
R. Pastor-Barriuso et al., "Transition models for change-point estimation in logistic regression," Statistics in Medicine, vol. 22, 2003, pp. 1141-1162.
S. H. Paek et al., "Hearing preservation after gamma knife stereotactic radiosurgery of vestibular schwannoma," Cancer, vol. 104, No. 3, Aug. 1, 2005, pp. 580-590.
J. K. Liu et al., "Pituitary Apoplexy," Seminars in Neurosurgery, vol. 12, No. 3, 2001, pp. 315-320.
G. Tanaka et al., "Bifurcation analysis on a hybrid systems model of intermittent hormonal therapy for prostate cancer," Physics D 237, 2008, pp. 2616-2627.
L. Chen et al., "Detecting early-warning signals for sudden deterioration of complex diseases by dynamical network biomarkers," Scientific Reports, 2: 342, Mar. 29, 2012, pp. 1-8.
Rui Liu, et al., "Identifying critical transitions and their leading biomolecular networks in complex diseases," Scientific Reports, vol. 2, Dec. 10, 2012, pp. 1-9.
Rui Liu, et al., "The Early Warning Signal of Complex Diseases Based on the Network Transition Entropy," 2011 IEEE International Conference on Systems Biology (ISB), Sep. 2, 2011, pp. 362-367.
Supplementary European Search Report dated Oct. 13, 2015, issued for the European patent application No. 13849648 4.

\* cited by examiner

Figure 2

| Type | Node | State transition for the center node | SNE for local netwok |
|---|---|---|---|
| 1 | DNB | $P(\|z(t) - z(t-1)\| > d) \to 1$ | Decreases drastically to 0 |
| 2 | DNB | $P(\|z(t) - z(t-1)\| > d) \to 1$ | Decreases |
| 3 | non DNB | $P(\|z(t) - z(t-1)\| > d) \to \beta$ | Decreases |
| 4 | non DNB | $P(\|z(t) - z(t-1)\| > d) \to \beta$ | Has no significant change |

DETECTION DEVICE, METHOD, AND PROGRAM FOR ASSISTING NETWORK ENTROPY-BASED DETECTION OF PRECURSOR TO STATE TRANSITION OF BIOLOGICAL OBJECT

TECHNICAL FIELD

The present invention relates to detection devices, methods, and programs for assisting detection of a precursor to a state transition of a biological object to be measured, based on measured data of a plurality of factors obtained by measurement on the biological object.

BACKGROUND ART

It has been identified that a sudden change of a system state exists widely in ecosystems, climate systems, and economics. Such a change often occurs at a critical threshold, or the so-called "tipping point", at which the system shifts abruptly from one state to another. Evidence has been found suggesting that the similar phenomena exist in clinical medicine, that is, during the progression of many complex diseases, e.g., in chronical diseases such as cancer, the deterioration is not necessarily smooth but abrupt (see, for example, non-patent documents 1 to 5). In other words, there exists a sudden catastrophic shift during the process of gradual health deterioration that results in a drastic transition from a healthy, stable state to a disease state. In order to describe the underlying dynamical mechanism of complex diseases, their evolutions are often modeled as time-dependent nonlinear dynamical systems, in which the abrupt deterioration is viewed as the phase transition at a bifurcation point, e.g., for cancer and, asthma attacks.

FIG. 1 is a schematic illustration of the dynamical features of disease progression from a normal state to a disease state through a pre-disease state. Portions (b), (c), and (d) of FIG. 1 are graphs of a potential function representing the stability of the aforementioned system during the progression process with the state variable on the horizontal axis and the values of the potential function on the vertical axis.

(a) Deterioration progress of disease.

(b) The normal state is a steady state or a minimum of a potential function, representing a relatively healthy stage.

(c) The pre-disease state is situated immediately before the tipping point and is the limit of the normal state but with a lower recovery rate from small perturbations. At this stage, the system is sensitive to external stimuli and still reversible to the normal state when appropriately interfered with, but a small change in the parameters of the system may suffice to drive the system into collapse, which often implies a large phase transition to the disease state.

(d) The disease state is the other stable state or a minimum of the potential function, where the disease has seriously deteriorated and thus the system is usually irreversible to the normal state.

Therefore, if the pre-disease state is detected, and the patient is notified of his/her progression process being in a transition to a disease state before the disease state actually arrives, it is likely that the patient can recover from the pre-disease state to the normal state if appropriately treated.

In other words, if the tipping point (critical threshold) is detected, a state transition becomes predictable, which enables an early diagnosis of a disease. However, in the case of complex diseases, it is notably hard to predict such critical transitions for the following reasons.

First, because a pre-disease state is a limit of the normal state, the state of the system may show little apparent change before the tipping point is reached. Thus, the diagnosis by traditional biomarkers and snapshot static measurements may not be effective to distinguish those two states (FIGS. 1b, c).

Second, despite considerable research efforts, no reliable disease model has been developed to accurately detect the early-warning signals. In particular, deterioration processes may be considerably different even for the same subtype of a disease, depending on individual variations, which makes model-based prediction methods fail for many cases.

Third and most importantly, detecting the pre-disease state must be an individual-based prediction, however, usually there are only a few of samples available for each individual, unlike many other complex systems that are measured over a long term with a large number of samples.

To address these issues, the inventors of the present invention proposed a method of detecting a biomarker candidate that serves as an early-warning signal indicating a pre-disease state that precedes a transition from a normal state to a disease state (see non-patent document 7). The technique enables an early diagnosis of a disease by detecting a dynamical network biomarker (DNB) that occurs immediately before a transition to a disease state.

CITATION LIST

Non-Patent Literature

Non-patent Document 1: "Self-organized patchiness in asthma as a prelude to catastrophic shifts" (U.K.), by Venegas, J. G., et al., Nature, Nature Publishing Group, 2005, Vol. 434, pp. 777-782.

Non-patent Document 2: "Prediction of epileptic seizures: are nonlinear methods relevant" (U.K.), by McSharry, P. E., Smith, L. A., and Tarassenko, L, Nature Medicine, Nature Publishing Group, 2003, Vol. 9, pp. 241-242.

Non-patent Document 3: "Transition models for change-point estimation in logistic regression" (U.S.A.), by Roberto, P. B., Eliseo, G., and Josef, C., Statistics in Medicine, Wiley-Blackwell, 2003, Vol. 22, pp. 1141-1162.

Non-patent Document 4: "Hearing preservation after gamma knife stereotactic radiosurgery of vestibular schwannoma" (U.S.A.), by Paek, S., et al., Cancer, Wiley-Blackwell, 2005, Vol. 1040, pp. 580-590.

Non-patent Document 5: "Pituitary Apoplexy" (U.S.A.), by Liu, J. K., Rovit, R. L., and Couldwell, W. T., Seminars in neurosurgery, Thieme, 2001, Vol. 12, pp. 315-320.

Non-patent Document 6: "Bifurcation analysis on a hybrid systems model of intermittent hormonal therapy for prostate cancer" (U.S.A.), by Tanaka, G., Tsumoto, K., Tsuji, S., and Aihara, K., Physical Review, American Physical Society, 2008, Vol. 237, pp. 2616-2627.

Non-patent Document 7: "Detecting early-warning signals for sudden deterioration of complex diseases by dynamical network biomarkers" by Luonan Chen, Rui Liu, Zhi-Ping Liu, Meiyi Li, and Kazuyuki Aihara, Scientific Reports, Mar. 29, 2012, the Internet (URL: http://www-.natureasia.com/ja-jp/srep/abstracts/35129).

SUMMARY OF THE INVENTION

Problems to be Solved by the Invention

As mentioned earlier, there is a societal demand for propositions of various detection methods for a pre-disease state that are effective to an early detection and treatment of a disease. The method for detecting a dynamical network biomarker (DNB) shown in non-patent document 7 may not achieve high detection accuracy due to noise in gene and other data obtained by measurement from biological samples. In addition, a huge amount of computation is needed to sift through large amounts of high-throughput data to detect a DNB candidate that satisfies conditions to qualify as a DNB.

The present invention, conceived in view of these issues, assumes that the state changes of a targeted factor and a connecting factor that dynamically connects directly to the targeted factor would form a local network entropy in a transition state to detect a pre-disease state that precedes a transition to a disease state based on the local network entropy. The present invention hence has an object to provide a device, method, and program capable of detecting a pre-disease state by a new technique.

Solution to Problem

A detection device in accordance with the present invention, to achieve the object, is a detection device for assisting detection of a precursor to a state transition of a biological object to be measured, based on measured data of a plurality of factors obtained by measurement on the biological object, the device including: selection means for selecting those factors for which the measured data shows a time-dependent change beyond a predetermined criterion; microscopic calculation means for calculating, for each factor, a microscopic entropy as understood in statistical mechanics between that factor and every neighboring factor thereof in a network representative of dynamical coupling among the factors obtained based on a correlation of the factors selected by the selection means; and detection means for detecting a factor as a precursor to a state transition when the microscopic entropy calculated by the microscopic calculation means shows a decrease beyond a predetermined detection criterion.

The detection device with these features is capable of assisting the detection of a precursor to a state transition of a biological object, based on microscopic entropy calculated based on statistical mechanics, in a network representative of dynamical coupling among multiple factors (state of biological object).

The detection device further includes: choosing means for choosing, as a candidate for a biomarker, a factor for which the microscopic entropy calculated by the microscopic calculation means shows a decrease beyond a predetermined choosing criterion, the biomarker being an index of a symptom of a biological object, wherein the detection means detects a factor as a precursor to a state transition when the microscopic entropy for the factor chosen by the choosing means shows a decrease beyond a predetermined detection criterion.

This arrangement narrows down the factors to be calculated, thereby reducing interference by noise for improved detection accuracy. Computation is also decreased, which reduces process load and allows for increased calculation speed.

The detection device further includes: macroscopic calculation means for statistically calculating a macroscopic entropy based on the microscopic entropy calculated for each factor by the microscopic calculation means, the macroscopic entropy being a representative value for all the selected factors, wherein the detection means detects a factor as a precursor to a state transition if the macroscopic entropy calculated by the macroscopic calculation means shows a decrease beyond a first detection criterion and the microscopic entropy calculated by the microscopic calculation means shows a decrease beyond a second detection criterion.

This arrangement enables macroscopic entropy-based detection of a state in which the entire system is unstable.

The detection device further includes means for accessing a database that stores interactions among the factors, wherein the microscopic calculation means includes means for deriving the network representative of dynamical coupling among the factors based on the interactions among the factors stored in the database.

This arrangement enables a network to be built based on the relationship among the factors.

The detection device may be such that the microscopic calculation means calculates, for each factor, a microscopic entropy based on a total sum of products of a probability of the measured data and a logarithm of the probability based on a probability density function that represents a distribution of a state change in measured data for all the neighboring factors.

This arrangement enables the entropy in the context of statistical mechanics and information theory to be used as a network entropy.

The detection device may be such that the microscopic calculation means, for each factor, binarizes the measured data according to magnitude of a change relative to a threshold determined based on an earlier perturbation, evaluates the probability density function assuming that the binarized measured data follows a multivariate normal distribution, and calculates a probability of the measured data that follows a stationary distribution based on a transition probability obtained by multiple integration of the evaluated probability density function.

This arrangement enables the network entropy to be calculated based on large changes of factors.

The detection device further includes difference verification means for verifying whether or not the measured data for each factor has significantly changed with time, wherein the selection means selects a factor verified to have significantly changed with time.

This arrangement enables selection of a factor that has shown noticeable changes.

The detection device may be such that the plurality of factors include a gene-related measured item, a protein-related measured item, or a metabolite-related measured item.

When the factors are genes, proteins, or metabolites, this arrangement enables quantitative observations of biological changes of a biological object.

A detection method in accordance with the present invention is a detection method using a detection device for assisting detection of a precursor to a state transition of a biological object to be measured, based on measured data of a plurality of factors obtained by measurement on the biological object, the detection device implementing: the selection step of selecting those factors for which the measured data shows a time-dependent change beyond a predetermined criterion; the microscopic calculation step of calculating, for each factor, a microscopic entropy as understood in statistical mechanics between that factor and every neighboring factor thereof in a network representative of dynamical coupling among the factors obtained based on a correlation of the factors selected by the selection means; and the detection step of detecting a factor as a precursor to a state transition when the microscopic entropy calculated by the microscopic calculation means shows a decrease beyond a predetermined detection criterion.

The detection method with these features is capable of assisting the detection of a precursor to a state transition of a biological object, based on microscopic entropy calculated based on statistical mechanics, in a network representative of dynamical coupling among multiple factors (state of biological object).

A detection program in accordance with the present invention is detection program for causing a computer to assist detection of a precursor to a state transition of a biological object to be measured, based on measured data of a plurality of factors obtained by measurement on the biological object, the computer implementing: the selection step of selecting those factors for which the measured data shows a time-dependent change beyond a predetermined criterion; the microscopic calculation step of calculating, for each factor, a microscopic entropy as understood in statistical mechanics between that factor and every neighboring factor thereof in a network representative of dynamical coupling among the factors obtained based on a correlation of the factors selected by the selection means; and the detection step of detecting a factor as a precursor to a state transition when the microscopic entropy calculated by the microscopic calculation means shows a decrease beyond a predetermined detection criterion.

When the detection program with these features is run on a computer, the computer operates as a detection device. The detection program is therefore capable of assisting the detection of a precursor to a state transition of a biological object, based on microscopic entropy calculated based on statistical mechanics, in a network representative of dynamical coupling among multiple factors (state of biological object).

Advantageous Effects of the Invention

The present invention collects biological samples from a subject to be diagnosed and calculates a microscopic entropy according to statistical mechanics for a network representative of dynamical coupling among multiple factors (state of biological object) based on measured data of multiple factors obtained by measurement on the collected biological samples. The present invention assists the detection of a precursor to a state transition of the biological object based on the calculated time-dependent changes of the entropy. These arrangements produce excellent effects including making a proposition of a new method of detecting a pre-disease state to realize an early detection and treatment of a disease.

BRIEF DESCRIPTION OF DRAWINGS

FIG. 2 is a table showing relationships between an SNE and a DNB.

DESCRIPTION OF EMBODIMENTS

Theoretical Foundation

Figure 1:
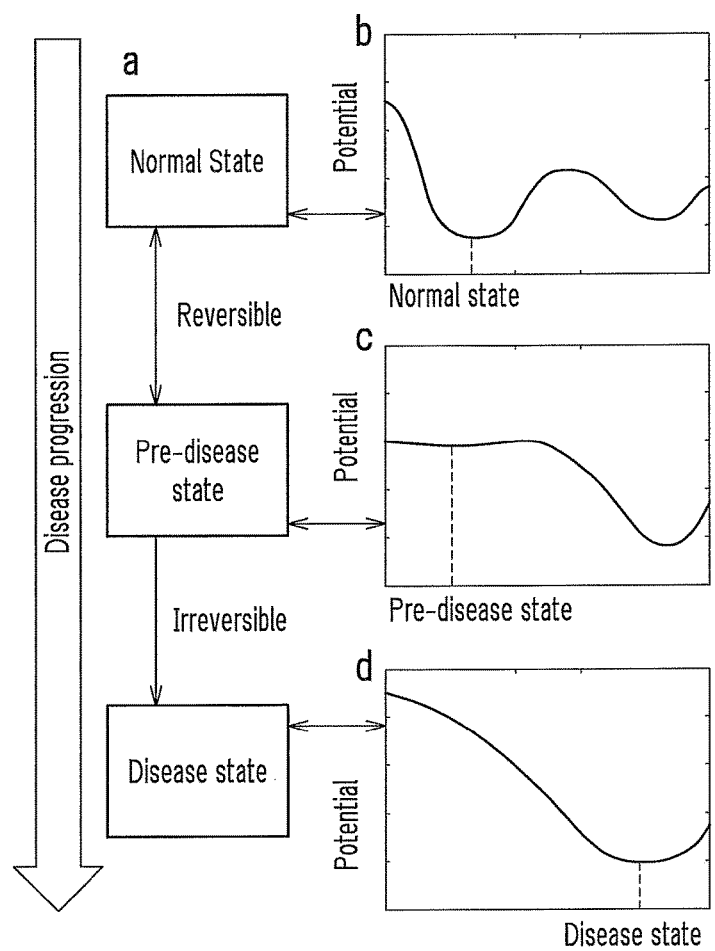
FIG. 1 is a schematic illustration of a progression process of a disease.

The inventors of the present invention have constructed a mathematical model of the chronological progression of a complex disease in accordance with bifurcation theory by using genomic high-throughput technology by which huge data (e.g., thousands of sets of data) (i.e., high-dimensional data) can be obtained from a single sample, in order to study deterioration progression mechanisms of a disease at molecular network level. The study has revealed the presence of a dynamical network biomarker (DNB) with which an immediately preceding bifurcation (sudden deterioration) state before a state transition can be detected in a pre-disease state. By using the dynamical network biomarker as an early-warning signal in a pre-disease state, even a small number of samples enable an early diagnosis of a complex disease without disease modeling.

Assume that the progression of a disease can be expressed by the dynamical system (hereinafter, "system (1)") represented by Mathematical Expression (1) below. ("Mathematical Expression" will be abbreviated as "Ex.")

$$Z(k+1)=f(Z(k);P) \qquad \text{Ex. (1)}$$

In Ex. (1), $Z(k)=(z_1(k), \ldots, z_n(k))$ represent observed data, i.e., concentrations of molecules (e.g., gene expressions, protein expressions, or metabolite expressions) at time k (k=0, 1, . . . ), e.g., hours or days, which are the variables describing the dynamical state of the system. P are parameters representing slowly changing factors, including genetic factors (e.g., SNP (single nucleotide polymorphism) and CNV (copy number variation)) and epigenetic factors (e.g., methylation and acetylation), which drive the system from one state (or attractor) to another.

The normal and disease states are described by respective fixed point attractors of the state equation $Z(k+1)=f(Z(k);P)$. Since the progression process of a complex disease has very complex dynamical features, the function f is a non-linear function of thousands of variables. Besides, the factors (parameters) P that drive system (1) are difficult to identify. It is therefore very difficult to construct a system model for the normal and disease states for analysis.

System (1) has a fixed point that has properties (A1) to (A3):

(A1) $Z^*$ is a fixed point of system (1) such that $Z^*=f(Z^*; P)$.

(A2) There is a value Pc such that one or a pair of the complex conjugate eigenvalues of the Jacobian matrix, $\partial f(Z;Pc)/\partial Z|Z=Z^*$, is equal to 1 in the modulus when P=Pc. Pc is a bifurcation threshold for the system.

(A3) When P≠Pc, the eigenvalues of system (1) are not always equal to 1 in the modulus.

From these properties, the inventors have theoretically found that when system (1) approaches a critical transition point, specific features emerge: when system (1) approaches a critical transition point, there emerges a dominant group (subnetwork) of some nodes of network (1) in which each node represents a different one of variables $z_1, \ldots, z_n$ of system (1). The dominant group that emerges near a critical transition point ideally has specific features (B1) to (B3).

(B1) If both $z_i$ and $z_j$ are in the dominant group, then $PCC(z_i,z_j) \to \pm 1$, while $SD(z_i) \to \infty$ and $SD(z_j) \to \infty$;

(B2) If $z_i$ is in the dominant group, but $z_j$ is not, then $PCC(z_i,z_j) \to 0$, while $SD(z_i) \to \infty$ and $SD(z_j)$ approaches a bounded value;

(B3) If neither $z_i$ nor $z_j$ is in the dominant group, then $PCC(z_i,z_j) \to \alpha$, $\alpha \in (-1,1)$, while both $SD(z_i)$ and $SD(z_j)$ approach a bounded value.

PCC(zi,zj) is a Pearson's correlation coefficient of zi with zj. SD(zi) and SD(zj) are standard deviations of zi and zj respectively.

In other words, in network (1), the emerging dominant group with specific features (B1) to (B3) can be regarded as an indicator that system (1) is in a critical transition state (pre-disease state). Therefore, a precursor to a critical transition for system (1) can be detected by detecting the dominant group. In other words, the dominant group can be regarded as an early-warning signal for a critical transition, that is, the pre-disease state that immediately precedes deterioration of a disease. In this manner, the pre-disease state can be identified by detecting only the dominant group which serves as an early-warning signal, without directly handling a mathematical model of system (1), no matter how complex system (1) becomes and even if the driving parameter factor is unknown. The identifying of the pre-disease state enables precautionary measures and an early treatment of a disease. As detailed in non-patent document 7, the inventors refer to the dominant group that serves as an early-warning signal for a pre-disease state as a dynamical network biomarker (hereinafter, abbreviated as a "DNB"). The DNB in non-patent document 7 is a network that, used as a biomarker, represents a logical, dynamical association that generates an effective association only at a particular timing.

As mentioned above, the DNB is a dominant group with a set of specific features (B1) to (B3), and when system (1) is in a pre-disease state, emerges as a subnetwork of some of the nodes of network (1). If the nodes $(z_i, \ldots, z_n)$ in network (1) are the factors to be measured on biological molecules (e.g., genes, proteins, metabolites), the DNB is a group (subnetwork) of factors related to some of the biological molecules that satisfy specific features (B1) to (B3).

A technique of detecting DNB candidates by directly using specific features (B1) to (B3) is already disclosed in non-patent document 7. The technique detects, from a biological sample, a DNB that serves as a warning for a transition to a disease state. Noise in measured data, however, will degrade the accuracy of the detection. In addition, it is necessary to detect a DNB that satisfy conditions (B1) to (B3) in large amounts of measured data. These constraints will lead to a huge amount of computation and poor efficiency of the detection.

To address these issues, the inventors suggest a method for detecting a pre-disease state by using a local network entropy that is based on a transition state. The method is capable of accurate and efficient DNB detection. Next, the method will be specifically described. The local network entropy described below is a microscopic entropy calculated according to statistical mechanics by focusing on one of nodes in a network representative of a logical, dynamical association that generates an effective association only at a particular timing. In the present application, a macroscopic entropy for the entire network is also calculated from local network entropies.

Local Network Entropy Based on Transition State

The dynamical behavior of system (1) mentioned above can be approximately represented by Ex. (2) when system (1) is near a tipping point.

$$Z(t+1)=A(P)Z(t)+\varepsilon(t) \quad \text{Ex. (2)}$$

In Ex. (2), $\varepsilon(t)$ is a Gaussian noise, P is a parameter vector that controls the Jacobian matrix A for a non-linear function f for system (1). Letting a change of Z be represented by $\Delta z_i(t)=z_i(t)-z_i(t-1)$ for $i=1, 2, \ldots, n$, conclusions (C1) and (C2) below can be proved based on bifurcation theory and center manifold theory.

(C1) When P is not in the vicinity of a critical transition point or a bifurcation point, the following holds.

For any node i and j including i=j, $\Delta z_i(t+T)$ is statistically independent of $\Delta z_j(t)$ where $i, j=1, 2, \ldots, n$.

(C2) When P approaches a critical transition point, the following holds.

If both i and j are in the dominant group, or DNB members, then there is a strong correlation between $\Delta z_i(t+T)$ and $\Delta z_j(t)$;

If neither i nor j is in the dominant group, then $\Delta z_i(t+T)$ is statistically independent of $\Delta z_j(t)$.

Based on conclusions (C1) and (C2) above, the inventors have focused on a transition state and found a method of more accurately and efficiently detecting a DNB by using a local network entropy (hereinafter, referred to as an "SNE" (state-transition-based local network entropy) where necessary). The following will describe the transition state-based concept of SNE and the relationship between an SNE and a DNB.

Transition State

Let a transition state be represented by $x_i(t)$ that satisfies conditions given as Ex. (3) and (4) below for an arbitrary variable $z_i$ at time t.

$$\text{If } |z_i(t)-z_i(t-1)|>d_i, x_i(t)=1 \quad \text{Ex. (3)}$$

$$\text{If } |z_i(t)-z_i(t-1)|\leq d_i, x_i(t)=0 \quad \text{Ex. (4)}$$

In Ex. (3) and (4), $d_i$ is a threshold by which to determine whether node i shows a large change at time t. A "transition state" of system (1) at time t in the present invention is defined as $X(t)=(x_1(t), \ldots, x_n(t))$. Properties (D1) and (D2) of a transition state are derived as below from the specific features of the DNB and conclusions (C1) and (C2) described above.

(D1) If both i and j are in the dominant group or DNB members, the correlation between the transition states $x_i(t+T)$ and $x_j(t)$ increases drastically, and $$p(x_i(t+T)=1|x_j(t)=\gamma) \to 1$$

$$p(x_i(t+T)=0|x_j(t)=\gamma) \to 0$$

where $\gamma \in \{0,1\}$, and p is a transition probability.

(D2) If neither i nor j is in the dominant group, or DNB members, then the transition state $x_i(t+T)$ is statistically independent of $x_j(t)$, and $$p(x_i(t+T)=\gamma_i|x_j(t)=\gamma_j)=p(x_i(t+T)=\gamma_i) \to \alpha$$

where $\gamma_i, \gamma_j \in \{0,1\}$, and $\alpha \in (0,1)$.

If the system is in a normal state, the system can quickly recover from a perturbation. In a pre-disease state, however, the system is sensitive even to a small perturbation. Therefore, the threshold $d_i$ needs to be specified so that it can distinguish between a "small change" in a normal state and a "large change" in a pre-disease state. In this embodiment, when the system is in a normal state ($t=t_0$), $p(|z_k(t_0)|>d_k)=\alpha$ at node k, and each threshold d is specified as in Ex. (5) below. It is judged whether or not there has occurred a large change, or a state transition, between the preceding state $z_i(t-1)$ and the state $z_i(t)$ for which the judgment is made, by using the thresholds d specified in Ex. (5). In Ex. (5), $i_1$, $i_2, \ldots, i_m$ represent m adjacent nodes linked to node i.

[Math. 1]

$$p(|z_i(t_0)|>d_i, |z_{i_1}(t_0)|>d_{i_1}, \ldots, |z_{i_m}(t_0)|>d_{i_m}) \leq \alpha \quad \text{Ex. (5)}$$

Each threshold $d_i$ is specified, for example, from samples collected in a normal state so that $\alpha=0.5$ for a perturbation in the normal state.

Local Network

If node i is linked with m nodes, that is, if node i has m adjacent nodes ($i_1, i_2, \ldots, i_m$), a local network is defined as a network centered on node i. When this is the case, the transition state at time t of the local network centered on node i is $X_i(t)=(X_i(t), X_{i1}(t), \ldots, X_{im}(t))$. $X_i(t)$ will be denoted X(t) with "i" being omitted throughout the following for simple and concise description of equations.

The links of each node i are specified based on interactions between nodes. For example, when a protein is used as a node, information may be used that is recorded in a database, such as the PPI (protein-protein interaction) representing interactions between proteins. These databases are obtainable from Web sites, for example, BioGrid (www.thebiogrid.org), TRED (www.rulai.cshl.edu/cgi-bin/TRED/), KEGG (www.gnome.jp/kegg), and HPRD (www.hprd.org). When a protein is used as a node, adjacent nodes, a local network including the adjacent nodes, and an entire network are specified based on a database, such as the PPI representing interactions between proteins. When another factor is used as a node, a database for that factor may be used.

Given the current state X(t) at time t for this local network, then at the next time point t+1 there is a total of $2^{m+1}$ possible state transitions (or possible transition states) for state X(t+1), each of which is a stochastic event that is denoted, respectively, as $\{A_u\}_{u=1, 2, \ldots, 2^{m+1}}$, where $$A_u = \{x_i = \gamma_0, x_{i1} = \gamma_1, \ldots, x_{im} = \gamma_m\} \quad \text{Ex. (6)}$$

with $\gamma_l \in \{0,1\}$, and $l \in \{0, 1, 2, \ldots, m\}$

Therefore, the discrete stochastic process in the local network is given by Ex. (7).

$$\{X(t+i)\}_{i=0,1,\ldots} = \{X(t), X(t+1), \ldots, X(t+i), \ldots\} \quad \text{Ex. (7)}$$

with $X(t+i)=A_u$, and $u \in \{1, 2, \ldots, 2^{m+1}\}$.

In other words, when system (1) is during the normal stage or during the pre-disease stage, the discrete stochastic process is a stochastic Markov process and defined or given by a Markov matrix $P=(p_{u,v})$, which describes the transition rates from state u to state v as in Ex. (8).

[Math. 2]

$$p_{u,v}(t) = Pr(X(t+1) = A_v \mid X(t) = A_u) \quad \text{Ex. (8)}$$

where $u, v \in \{1, 2, \ldots, 2^{m+1}\}$, $$\sum_v p_{u,v}(t) = 1,$$

Pr: Discrete Stochastic Process.

Local Network Entropy

Assume that the state transition matrix for a local network is stationary and does not change over a particular period. $p_{u,v}(t)$ is an element in row u and column v of the state transition matrix and denotes a transition probability between two arbitrary possible states Au and Av. Therefore, the stochastic process denoted by Ex. (9) is a stationary stochastic Markov process over a particular period (during the normal stage or during the pre-disease stage).

[Math. 3]

$$\text{Stochastic Process } \{X(t)\}_{t \in [t1, t2]} \quad \text{Ex. (9)}$$

There is a stationary distribution $\pi=(\pi_1, \ldots, \pi_{2^{m+1}})$ that satisfies Ex. (10).

[Math. 4]

$$\sum_v \pi_v p_{u,v} = \pi_u \quad \text{Ex. (10)}$$

Using this stationary distribution, the local network entropy denoted by Ex. (11) can be defined.

[Math. 5]

$$H_i(t) = H(x) = -\sum_{u,v} \pi_v p_{u,v} \log P_{u,v} \quad \text{Ex. (11)}$$

where, the subscript index "i" indicates the center node i of this local network, while X represents the state transition process $X(t), X(t+1), \ldots, X(t+T)$ of the local network. The local network entropy given by Ex. (11) is an extended concept of microscopic entropy as understood in statistical mechanics.

The local network entropy will be referred to as the SNE throughout the following. As mentioned above, the stochastic process $X(t), X(t+1), \ldots$ is a stochastic Markov process during a particular period. Therefore, Ex. (12) is derived from, for example, the properties of the Markov chains.

[Math. 6]

$$H_i(t) = H(x) =: \lim_{T \to \infty} \frac{1}{T} H(X(t), X(t+1), \ldots, X(t+T)) \quad \text{Ex. (12)}$$

Therefore, the SNE is a conditional entropy and may be termed a state transition-dependent average transition entropy. Hence, the SNE is denoted by Ex. (13).

$$H_i(t) = H(X(t)|X(t-1)) = H(X(t), X(t-1)) - H(X(t-1)) \quad \text{Ex. (13)}$$

The SNE has properties (E1) to (E3).

(E1) In a normal state (or a disease state), system (1) recovers from a small perturbation quickly because of high resilience, i.e., X(t) and X(t−1) are almost independent. It then follows that $$H(X(t), X(t-1)) \approx H(X(t)) + H(X(t-1)) > 0$$

Therefore, $$Hi(t) \approx H(X(t))$$

The SNE value does not decrease by large amounts.

(E2) By contrast, system (1) has difficulty recovering from a small perturbation in a pre-disease state because of low resilience, i.e., X(t) and X(t−1) are strongly correlated.

It follows that $$H(X(t),X(t-1)) \approx H(X(t-1))$$

Therefore, $$H_i(t) \approx 0$$

$H_i(t)$ then drastically decreases.

(E3) The average value of the SNEs of local networks may be taken as the SNE of the entire network. In other words, as shown in Ex. (14) below, H(t) denoting the SNE of an entire network of n nodes may be taken as the average value of Hi(t) denoting the SNEs of local networks centered on the nodes.

[Math. 7]

$$H(t) = \frac{1}{n} \sum_{i=1}^{n} H_i(t) \qquad \text{Ex. (14)}$$

The SNE of the entire network given in Ex. (14) is an extended concept of macroscopic entropy as understood in statistical mechanics.

The relationship between the SNE defined as above and a DNB as another method of detecting a pre-disease state will be described. The nodes in a network in the present application can be categorized into four types as below according to DNB-related relationships between each node and the other nodes.

Type 1 (DNB core node): A DNB core node is a DNB node that is linked with DNB nodes only.

Type 2 (DNB boundary node): A DNB boundary node is a DNB node that is linked with at least one non-DNB node.

Type 3 (non-DNB core node): A non-DNB core node is a non-DNB node that is linked with at least one DNB node.

Type 4 (non-DNB boundary node): A non-DNB boundary node is a non-DNB node that has no links with DNB nodes.

Let $H^{nor}(X)$ represent the SNEs in the normal state and $H^{pre}(X)$ represent the SNEs in the pre-disease state. $H^{nor}(X)$ and $H^{pre}(X)$ are given by Ex. (15) and (16) respectively.

[Math. 8]

$$H^{nor}(x) = -\sum_{u,v} \pi_u^{nor} p_{u,v}^{nor} \log p_{u,v}^{nor} \qquad \text{Ex. (15)}$$

where $$p^{nor}(x_i(t) = 1) = p^{nor}(|\Delta z_i| \geq d_i) = \alpha,$$
$$p^{nor}(x_i(t) = 0) = p^{nor}(|\Delta z_i| < d_i) = 1 - \alpha.$$

$$H^{pre}(x) = -\sum_{u,v} \pi_u^{pre} p_{u,v}^{pre} \log p_{u,v}^{pre} \qquad \text{Ex. (16)}$$

where $$p^{pre}(x_j(t) = 1) = p^{pre}(|\Delta z_j| \geq d_j) \rightarrow 1,$$
$$p^{pre}(x_j(t) = 0) = p^{pre}(|\Delta z_j| < d_j) \rightarrow 0.$$

FIG. 2 is a table showing relationships between an SNE and a DNB. FIG. 2 shows mathematical expressions, as well as relationships between the SNE and DNB as proved from the generic properties of the DNB for each type in association with the types of nodes, the state transitions for the center node, and the states of the local SNE when the system is near a critical transition.

In FIG. 2, ß is a constant such that ß∈(0,1). Specifically, in a local network with a center node of type 1 (DNB core node), the state transition for the center node is close to 1, and the SNE drastically decreases to 0; in a local network with a center node of type 2 (DNB boundary node), the state transition for the center node is close to 1, and the SNE decreases; in a local network with a center node of type 3 (non-DNB core node), the state transition for the center node is close to the predetermined constant ß, and the SNE decreases; and in a local network with a center node of type 4 (non-DNB boundary node), the state transition for the center node is close to the predetermined constant ß, and the SNE has no significant change.

Figure 3:
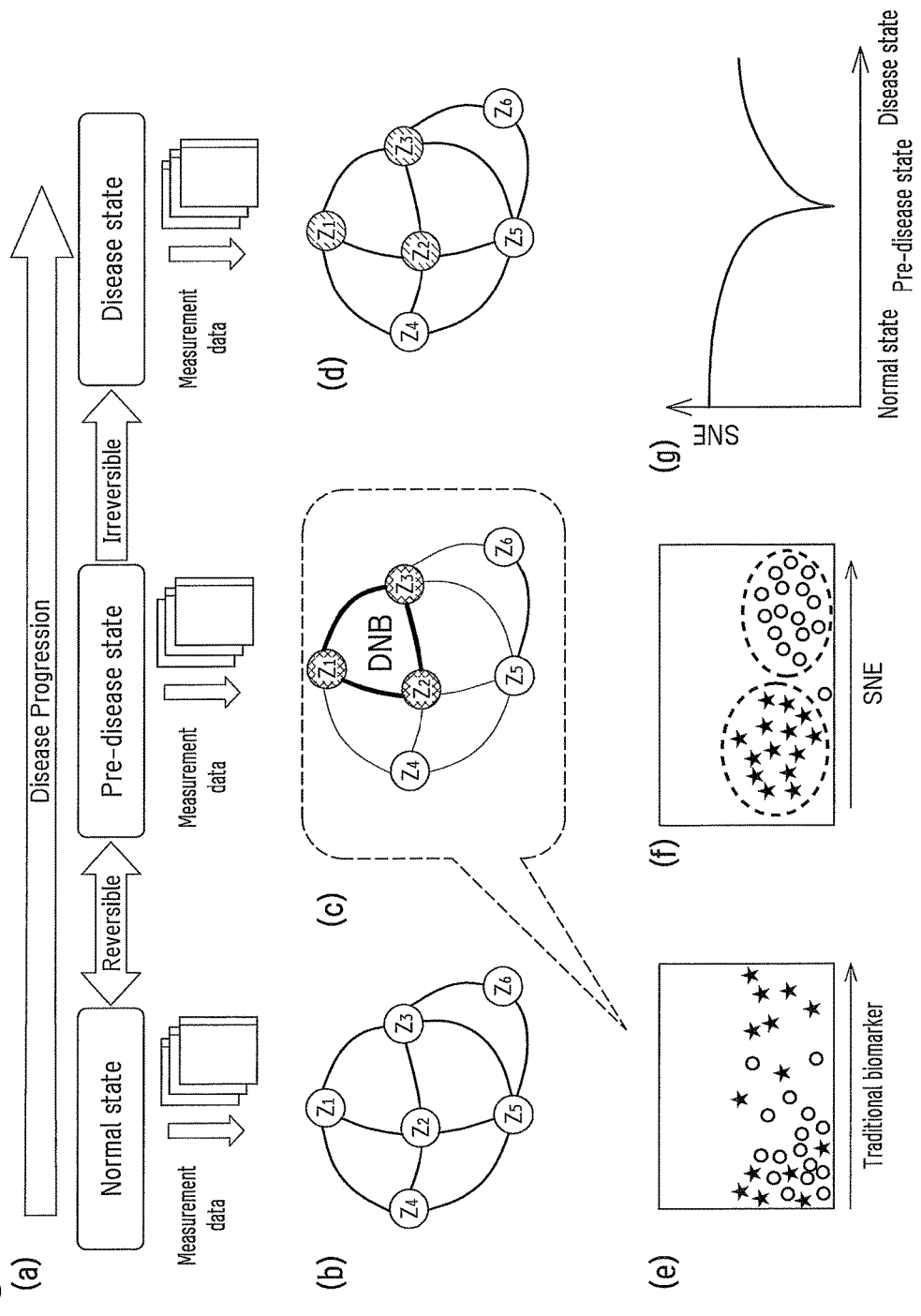
FIG. 3 is a schematic illustration of exemplary features of a DNB and an SNE in a progression process of a disease.

FIG. 3 is a schematic illustration of exemplary features of a DNB and an SNE in a progression process of a disease. FIG. 3 conceptually illustrates features of a DNB and an SNE in a progression process of a disease. FIG. 3 shows a network of nodes z1 to z6 representing, for example, genes.

Portion (a) of FIG. 3 shows a normal state, a pre-disease state, and a disease state, where the system can be reversed from the pre-disease state to the normal state, but can hardly be reversed from the disease state to the pre-disease state.

Portion (b) of FIG. 3 shows nodes z1 to z6 (represented by circles) in the normal state. Specifically, it shows the standard deviation (indicated by the density of oblique lines in the circle) of the nodes and correlation coefficients between the nodes.

Portion (c) of FIG. 3 shows nodes z1 to z6 in the pre-disease state, where the standard deviation of z1 to z3 is high (indicated by dense oblique lines in the circles), and the correlation coefficients between nodes z1 to z3 are high (indicated by thick linking lines), but their correlation coefficients with the other nodes are low (indicated by thin linking lines with the other nodes). Therefore, z1 to z3 (DNB members) become more prominent in the pre-disease state.

Portion (d) of FIG. 3 shows nodes z1 to z6 in the disease state, where the standard deviation of nodes z1 to z3 is slightly higher than in the normal state, but the correlation coefficients between nodes z1 to z6 are more or less equal to each other.

Portion (e) of FIG. 3 illustrates a diagnosis by means of a traditional biomarker and shows a traditional biomarker index on its horizontal axis, such as the concentration of a specific protein: the concentration or like index increases from left to right. As shown in (e) of FIG. 3, the diagnosis by means of a traditional biomarker is not capable of distinguishing clearly between the normal samples indicated by circles and the pre-disease samples indicated by stars in the pre-disease state.

Portion (f) of FIG. 3 shows, as an example, the samples in (e) of FIG. 3 being relocated by using the SNE as an index: the SNE decreases from left to right, giving an increasingly high level of warning. As shown in (f) of FIG. 3, the normal samples indicated by circles are separated clearly from the pre-disease samples indicated by stars by using the SNE. Therefore, the use of an SNE as an index enables detection of a pre-disease state.

Portion (g) of FIG. 3 is a graphical representation of changes of the average SNE of the network in a progression process of a disease, with time being plotted on the horizontal axis and SNE values being plotted on the vertical axis. The SNE value is high in the normal and disease states, indicating that the system has a high level of robustness, whereas the SNE value drastically decreases in the pre-disease state, indicating that the system has a low level of robustness.

Detection of Pre-Disease State by SNEs

As mentioned above, when the system approaches a state transition point, that is, when the system moves into a pre-disease state, a dominant group of DNB nodes emerges, pushing the system from the normal state to the disease state. If the SNEs of the local networks with their center nodes located at mutually different nodes i across the entire network are calculated at each sampling time t using the relationship between SNEs and DNBs given in the table of FIG. 2, a node where the SNE value drastically decreases can be detected as a DNB node. Furthermore, the average SNE across the entire network may be calculated from the calculated SNEs of the local networks. A drastic decrease of the average SNE indicates that there exists many DNB nodes and that a dominant group of DNB nodes is emerging, which enables a judgment that the system is in a pre-disease state. In addition, as shown in the table of FIG. 2, the SNE value does not increase at nodes of types 1 to 4. Therefore, if only those SNE values, of local networks, that have decreased are used in the calculation of an average SNE across the entire network, noise is prevented from interfering, possibly improving on detection accuracy. Besides, since the amount of computation is decreased, computation efficiency is improved.

Method for Detecting DNB

Figure 4:
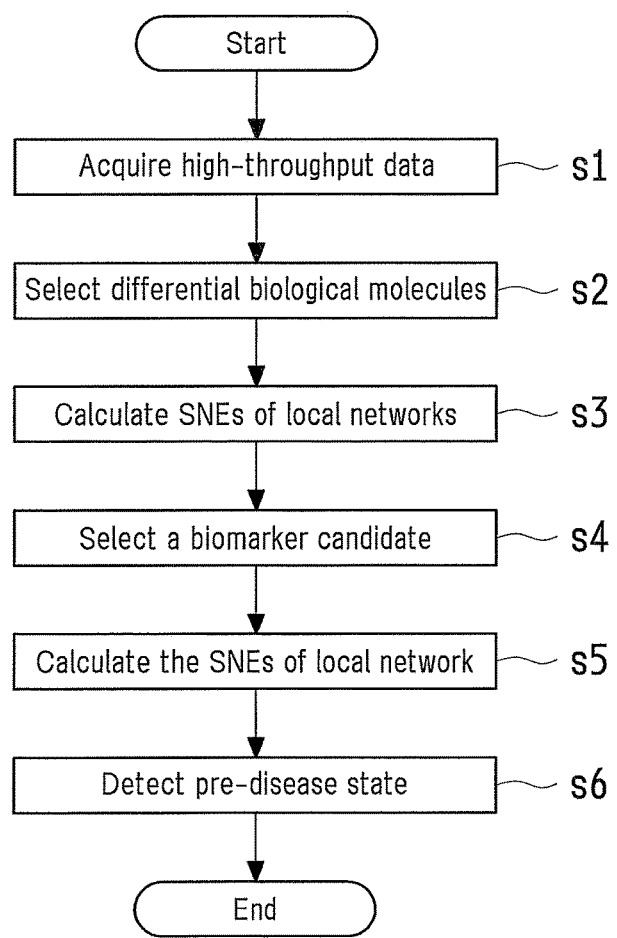
FIG. 4 is a flow chart depicting an exemplary method for detecting a DNB in accordance with an embodiment.

Next, a concrete method of detecting a pre-disease state by means of SNEs according to the aforementioned theories will be described. FIG. 4 is a flow chart depicting an exemplary method for detecting a pre-disease state in accordance with an embodiment. In the detection method in accordance with the present invention, it is first of all necessary to obtain measured data by measurement on a biological object. More than 20,000 gene expressions can be measured on one biological sample by a DNA chip or like high-throughput technology. For statistical analysis, in the present invention, multiple biological samples are collected at different times from an object to be measured. Measurement is then made on the collected biological samples, and the obtained measured data is aggregated for statistical data. The method for detecting a DNB in accordance with the present invention, as illustrated in FIG. 4, primarily involves a process of obtaining high-throughput data (s1), a process of selecting differential biological molecules (s2), a process of calculating the SNEs of local networks (s3), a process of selecting a biomarker candidate (s4), a process of calculating an average SNE across the entire network (s5), and a detection process of determining and detecting whether or not the system is in a pre-disease state (s6). Next will be described each of these processes in detail.

The process of obtaining high-throughput data in step s1 yields high-throughput physiological data, that is, measured data (e.g., microarray data) on expressions of biological molecules, from each target sample (case sample) and reference sample (control sample). A reference sample is, for example, a sample collected in advance from a patient who will undergo a medical checkup or a sample collected first during the course of collection, and is used as a control sample for the purpose of, for example, calibration of measuring instruments. A control sample is, although not essential, useful to exclude error factors and improve measurement reliability.

Figure 5:
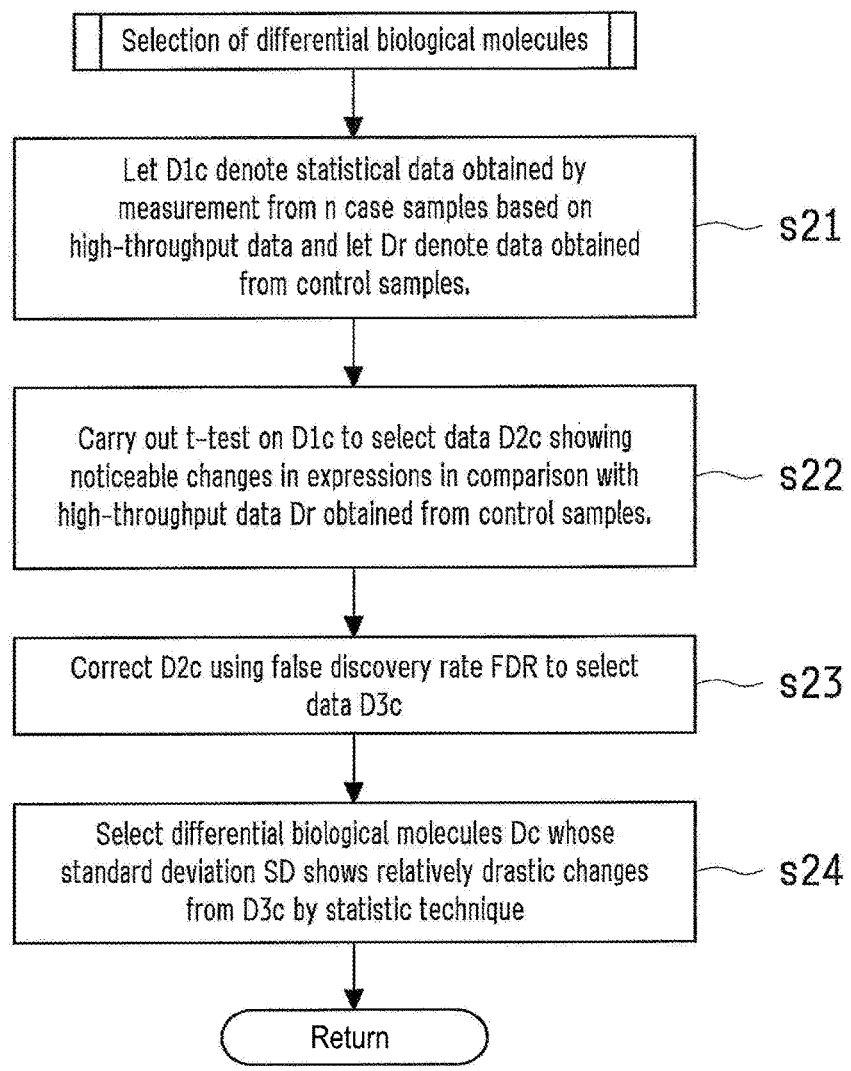
FIG. 5 is a flow chart depicting an exemplary selection process for differential biological molecules in accordance with an embodiment.

The process of selecting differential biological molecules in step s2 selects biological molecules whose expressions have noticeably changed. FIG. 5 is a flow chart depicting an exemplary process of selecting differential biological molecules in accordance with an embodiment. FIG. 5 shows in detail the process of selecting differential biological molecules in step s2 shown in FIG. 4.

As illustrated in FIG. 5, first, let D1$c$ denote statistical data obtained from the high-throughput data (expressions of biological molecules) that in turn is obtained by measurement from n case samples and Dr denote data obtained by measurement from control samples (s21). Next, the biological molecules D1$c$ from the case samples are subjected to a t-test to select biological molecules D2$c$ whose expressions have noticeably changed in comparison to the high-throughput data Dr obtained from the control samples (s22). T-test is given as an exemplary technique to select biological molecules D2$c$ whose expressions have noticeably changed in step s22; the technique is however by no means limited in any particular manner. Another test technique, such as U-test, may be used. Tests by such a non-parametric technique are especially effective when the population D1$c$ does not follow a normal distribution. In addition, in t-tests, the significance level $\alpha$ may be set, for example, to 0.05, 0.01, or another appropriate value.

Next, multiple comparisons or multiple t-tests are corrected for the biological molecules D2$c$ obtained from the case samples using a FDR (false discovery rate) to select corrected case sample gene or protein data D3$c$ (s23). Next, Dc whose standard deviation SD has relatively drastically changed are selected, as differential biological molecules, from the corrected case sample gene or protein data D3$c$ by a two-fold change method (s24). The selected differential biological molecules Dc not only have a noticeable difference from the biological molecules Dr obtained from the control samples, but also greatly deviate from their own average value. In step s23, t-test is again not the only feasible testing technique.

Figure 6:
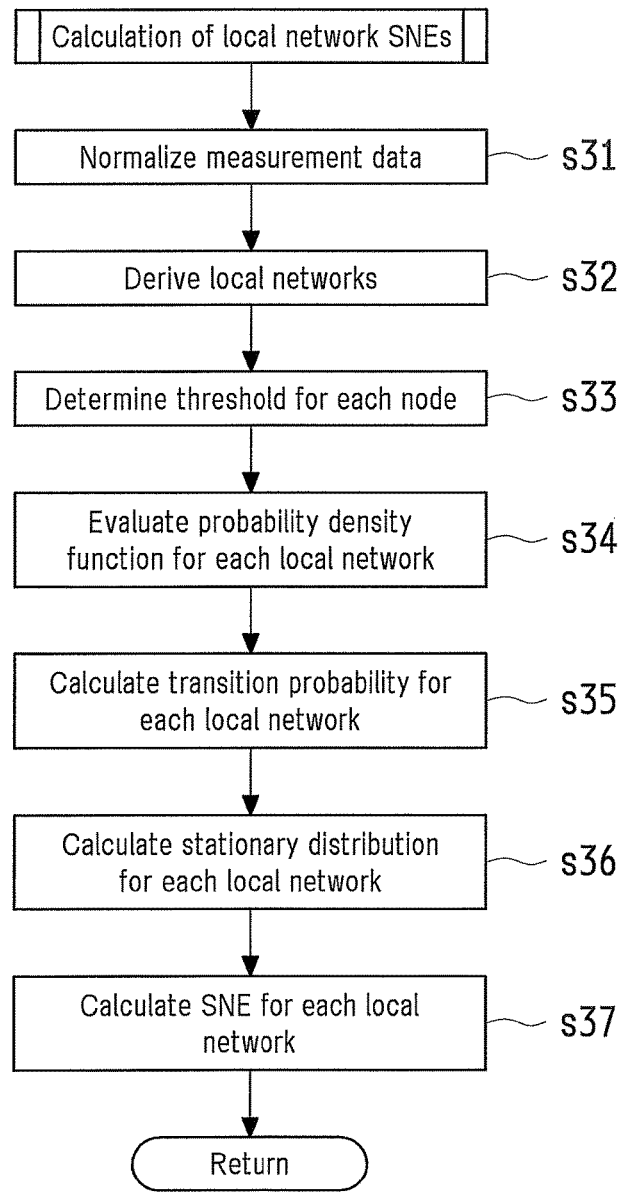
FIG. 6 is a flow chart depicting an exemplary SNE calculation process for a local network in accordance with an embodiment.

Next, the process of calculating the SNEs of local networks (step s3 in FIG. 4) is carried out. FIG. 6 is a flow chart depicting an exemplary SNE calculation process for a local network in accordance with an embodiment. First, the measured data on the differential biological molecules Dc selected in step s24 is normalized using Ex. (17) below (step s31). The data normalized by Ex. (17) is used in next and subsequent calculations.

$$A=(D\text{case}-\text{mean}(N\text{control}))/\text{SD}(N\text{control}) \qquad \text{Ex. (17)}$$

where Dcase is measured data of, for example, gene or protein concentration, mean (Ncontrol) is an average value for control samples, and SD (Ncontrol) is the standard deviation for the control samples.

The local networks each with a center node denoting a biological molecule in the differential biological molecules Dc selected in step s24 are derived using PPI or another similar database (step s32).

A set of thresholds $d=\{d_1, \ldots, d_N\}$ is determined for the N selected center nodes (step s33). The set of thresholds d determined for the nodes in step s33 is used in Ex. (3) and (4) to determine a transition state and is determined so that $\alpha$ becomes equal to, for example, 0.5, where $\alpha$ is given by $p(|z_k(t_1)|>d_k)=\alpha$ at node k for a sample collected at time $t_1$ (normal state) to a perturbation in the normal state.

The probability density function f defined in Ex. (18) is evaluated for each of the derived local networks (step s34). The probability density function f, in step s34, is evaluated using data obtained by normalizing measured data and then binarizing the normalized data with the set of thresholds d.

[Math. 9]

$$f_{t_k}(Z) = \frac{1}{(2\pi)^{k/2}|\Sigma(t_k)|^{1/2}} \exp\left(-\frac{1}{2}(Z-u(t_k))^T \Sigma(t_k)^{-1}(Z-u(t_k))\right) \quad \text{Ex. (18)}$$

Ex. (18) gives a probability density function f on an assumption that samples with k nodes follow a multivariate normal distribution. In Ex. (18), $Z=(z_1, \ldots, z_N)$, and the average values for the local networks at time t are $\mu(t_k)=(\mu_1(t_k), \ldots, \mu_N(t_k))$. In addition, $\Sigma\mu(t_k)$ is a covariance matrix for the local networks. The probability density function f defined in Ex. (18) is subjected to a multiple integration over different integration domains to calculate the transition probability $p_{u,v}(t_k)$ for each local network at time tk as shown in Ex. (19) below (step s35).

[Math. 10]

$$p_{u,v(t_k)} = Pr(X(t_k) = A_v \mid X(t_{k-1}) = A_u) \quad \text{Ex. (19)}$$

$$= \frac{Pr(X(t_k) = A_v, X(t_{k-1}) = A_u)}{Pr(X(t_{k-1}) = A_u)}$$

$$= \frac{\int \cdots \int_{Z\in\Omega_u, \tilde{Z}\in\Omega_v} f_{t_k}(Z,\tilde{Z}) dz_1 \ldots dz_N d\tilde{z}_1 \ldots d\tilde{z}_N}{\int \cdots \int_{Z\in\Omega_u} f_{t_k}(Z) dz_1 \ldots dz_N}$$

In Ex. (19), $Z=(z_1, \ldots, z_N)$, $\tilde{Z}=(\tilde{z}_1, \ldots, \tilde{z}_N)$, $\Omega u$ and $\Omega v$ are the integration domains respectively corresponding to states Au and Av (absent typographical constrains, "$\tilde{Z}$" should appear as Z with a " ~ " on top of it). The transition probability $p_{u,v}(t_k)$ is determined in Ex. (19) by conditional multivariate normal distributions or Gaussian Kernel estimators. Furthermore, the stationary distribution $\pi_v(t_k)$ at time $t_k$ is calculated from the transition probability $p_{u,v}(t_k)$ as in Ex. (20) (step s36).

[Math. 11]

$$\sum_v \pi_v(t_k) p_{u,v}(t_k) = \pi_u(t_k) \quad \text{Ex. (20)}$$

Next, the entropy H ($t_k$) of each local network centered on a node i (i=1, . . . , N) at time $t_k$ is calculated according to Ex. (21) using the transition probability $p_{u,v}$(tk) and stationary distribution $\pi_v$(tk) obtained by calculation (step s37).

[Math. 12]

$$H_i(t_k) = -\sum_{u,v} \pi_v(t_k) p_{u,v}(t_k) \log P_{u,v}(t_k) \quad \text{Ex. (21)}$$

Figure 7:
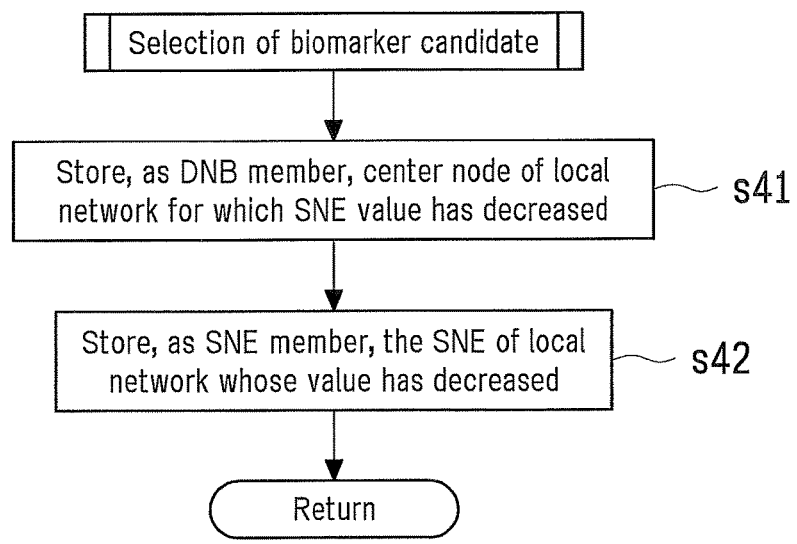
FIG. 7 is a flow chart depicting an exemplary selection process for a biomarker candidate in accordance with an embodiment.

Next, a biomarker candidate is selected (step s4 in FIG. 4). FIG. 7 is a flow chart depicting an exemplary selection process for a biomarker candidate in accordance with an embodiment. In the process of selecting a biomarker candidate, which local networks have shown a drastic decrease to 0 in their SNE values is determined based on the calculation in step s36 from a time-dependent change that occurs from time t–1 (normal state) to time t at which it is determined whether or not the system is in a pre-disease state. The center nodes of these local networks are recorded as DNB members (step s41). Furthermore, the SNEs of the local networks having shown a decrease in their SNE values are recorded as members of the "SNE group" (step s42). The set of steps s41 and s42 chooses a factor as a biomarker candidate that serves as an index of a symptom of a biological object if the SNE of a local network for that factor decreases beyond a predetermined choosing criterion. The center nodes (step s41) and the SNEs (step s42) are recorded in a storage or memory unit of a detection device (described later in detail).

Next, the average SNE across the entire network is calculated (step s5 in FIG. 4). In step s5, the average SNE across the entire network is calculated from only the SNEs that are members of the SNE group recorded at each predetermined time in step s42 according to Ex. (14). Use of only the SNEs that are members of the SNE group prevents interference by noise, improving accuracy and reducing computation.

A detection process for a pre-disease state is then carried out (step s6 in FIG. 4). Specifically, it is determined whether or not in the SNEs of the entire network calculated at the predetermined times in step s5, there exists an SNE whose value has drastically decreased beyond a predetermined detection criterion. If it is determined that there exists an SNE whose value has drastically decreased in such a manner, it is determined, at the time when the SNE has decreased, that the system is in a pre-disease state. In other words, it is detected that the system is in the pre-disease state. On the other hand, if it is determined that there exists no SNE whose value has drastically decreased, in other words, if the decrease does not exceed the predetermined detection criterion, it is determined that the system is not in the pre-disease state. When there exists an SNE whose value has drastically decreased in the above manner, the detection can assist a medical diagnosis that the system is likely be in the pre-disease state and may be used to encourage a checkup or other diagnosis.

Detection Device

Figure 8:
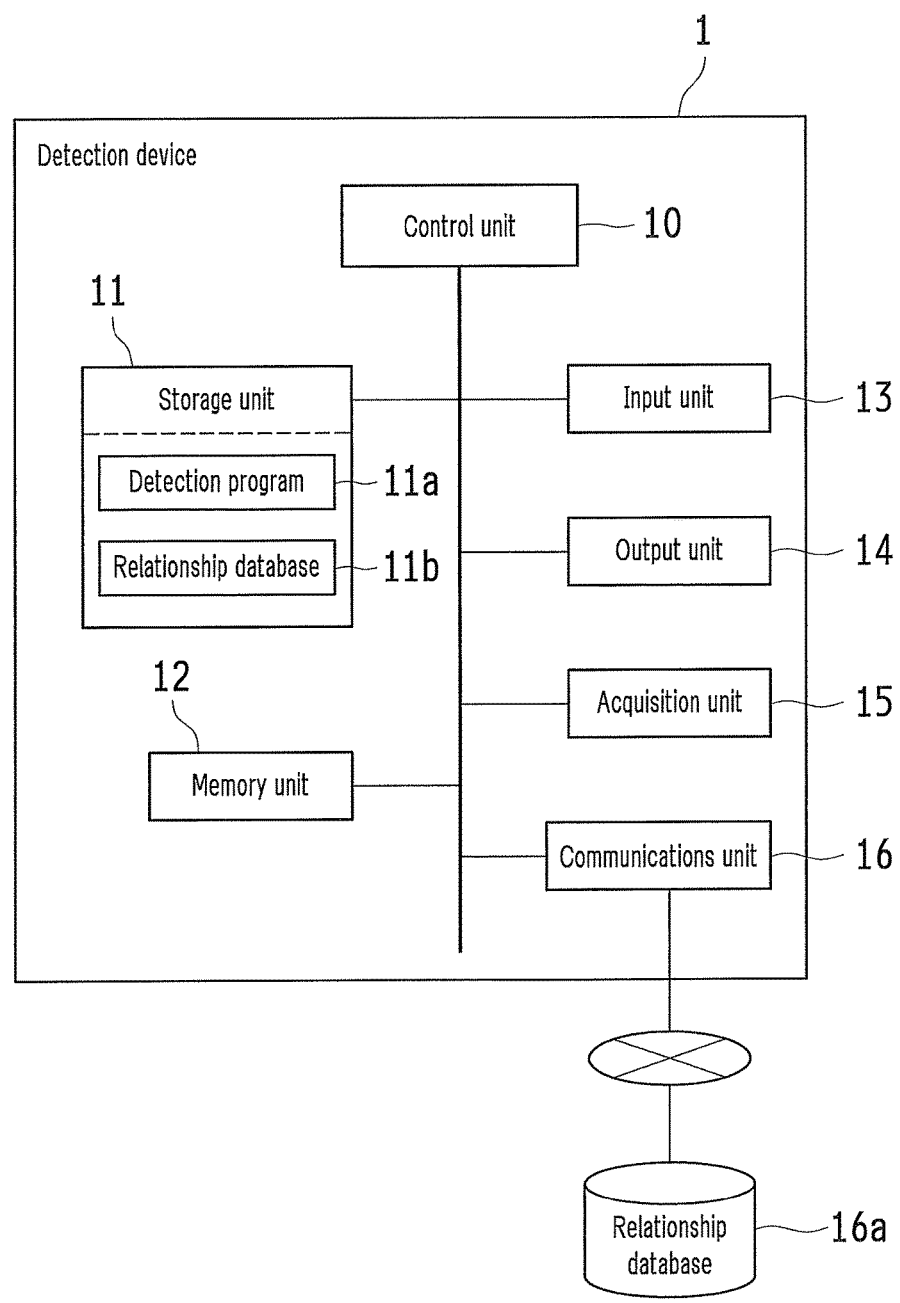
FIG. 8 is a block diagram illustrating an exemplary structure of a detection device in accordance with the present invention.

The method of an SNE-based detection of a pre-disease state described in detail above is an embodiment of the present invention and may be implemented on a computer-based detection device. FIG. 8 is a block diagram illustrating an exemplary structure of a detection device in accordance with the present invention. The detection device 1 in FIG. 8 may be realized using a personal computer, a client computer connected to a server computer, or any other kind of computer. The detection device 1 includes, for example, a control unit 10, a storage unit 11, a memory unit 12, an input unit 13, an output unit 14, an acquisition unit 15, and a communications unit 16.

The control unit 10 is composed of a CPU (central processing unit) and other circuitry and is a mechanism controlling the whole detection device 1.

The storage unit 11 is a non-volatile auxiliary storage mechanism, such as a HDD (hard disk drive) or a like magnetic storage mechanism or an SSD (solid state disk) or a like non-volatile semiconductor storage mechanism. The storage unit 11 stores a detection program 11a in accordance with the present invention and other various programs and data. The storage unit 11 also stores a relationship database 11b representing the relationship between the factors used in the detection of a pre-disease state. The relationship database 11b may be a PPI or like database representing protein-to-protein interactions (factor-to-factor relationships). The control unit 10 accesses the relationship database 11b for stored factor-to-factor relationships.

The memory unit 12 is a volatile, main memory mechanism, such as an SDRAM (synchronous dynamical random access memory) or an SRAM (static random access memory).

The input unit 13 is an input mechanism including hardware (e.g., a keyboard and a mouse) and software (e.g., a driver).

The output unit 14 is an output mechanism including hardware (e.g., a monitor and a printer) and software (e.g., a driver).

The acquisition unit 15 is a mechanism for external acquisition of various data: specifically, various hardware, such as a LAN (local area network) port for acquiring data over an internal communications network (e.g., an LAN) or a port for connection to a dedicated line (e.g., a parallel cable to be connected to measuring instruments) and software (e.g., a driver).

The communications unit 16 may be a combination of hardware, such as a LAN port for acquiring data over an external communications network (e.g., the Internet), and software (e.g., a driver). If the acquisition unit 15 is built around a LAN port, the acquisition unit 15 and the communications unit 16 may be combined into a single unit. The communications unit 16 is capable of acquiring information from the relationship database 16a stored in an external storage device (e.g., a Web server connected over an external communications network). In other words, the control unit 10 is capable of accessing the relationship database 16a for stored factor-to-factor relationships.

By loading the detection program 11a stored in the storage unit 11 into the memory unit 12 and running the detection program 11a under the control of the control unit 10, the computer implements various procedures stipulated in the detection program 11a to function as the detection device 1 in accordance with the present invention. The storage unit 11 and the memory unit 12, despite being separately provided for the sake of convenience, have similar functions of storing various information: which of the mechanisms should store which information may be determined in a suitable manner according to device specifications, usage, etc.

Figure 9:
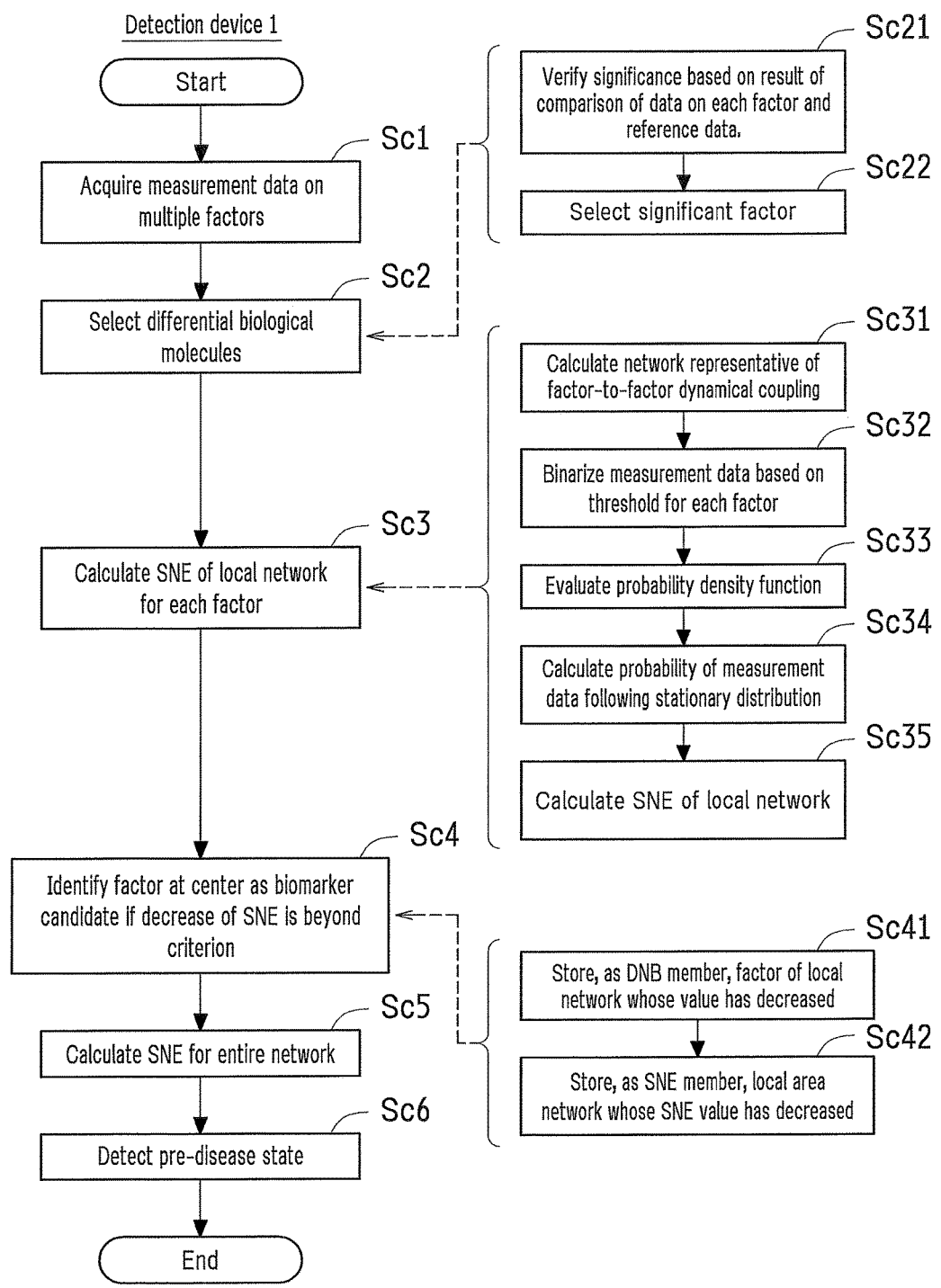
FIG. 9 is a flow chart depicting an exemplary detection process for a state transition of a biological object using a detection device in accordance with the present invention.

FIG. 9 is a flow chart depicting an exemplary process of detecting a state transition of a biological object by the detection device 1 in accordance with the present invention. The detection device 1 in accordance with the present invention implements the aforementioned SNE-based detection process for a pre-disease state. The control unit 10 in the detection device 1 acquires, through the acquisition unit 15, measured data on a plurality of factors obtained by measurement on a biological object (Sc1). Step Sc1 corresponds to the process of obtaining high-throughput data identified as step s1 in FIG. 4. Note that although the term "factor" is used in this context to indicate that it is an object for computer processing, the "factor" here refers to a gene-related measured item, a protein-related measured item, a metabolite-related measured item, or another measured item that could be a node for a DNB.

The control unit 10 verifies whether or not each measured data set obtained for a factor has significantly changed with time and selects differential biological molecules based on a result of the verification (Sc2). Step Sc2 corresponds to the process of selecting differential biological molecules identified as step s2 in FIG. 4.

Therefore, in step Sc2, the control unit 10 verifies significance based on a result of comparison of the measured data for each factor and the reference data predetermined for each factor and each time series (Sc21) and selects a factor that is verified to have significantly changed with time (Sc22). In other words, the steps shown in FIG. 5 are implemented in step Sc2. The data processed as reference data by the detection device 1 is control samples. For example, the detection device 1 is set up to take samples that are obtained first as control samples to handle the samples as reference data based on this setup.

The control unit 10 calculates the SNE of a local network for each selected factor, as a microscopic entropy as understood in statistical mechanics between that factor and neighboring selected factors, in a network representative of dynamical coupling between factors obtained based on a correlation of the time-dependent changes of the factors (Sc3). Step Sc3 corresponds to the process of calculating the SNE of a local network identified as step s3 in FIG. 4.

Therefore, in step Sc3, the control unit 10 accesses the relationship database 11b or 16a and derives a network representative of dynamical coupling between factors based on the stored interactions between the factors (Sc31). Furthermore, the control unit 10 binarizes the measured data for each factor according to the magnitude of a change relative to the threshold that is determined based on earlier perturbations (Sc32), evaluates the probability density function assuming that the binarized measured data follows a multivariate normal distribution (Sc33), and calculates the probability of the measured data that follows a stationary distribution, based on the transition probability obtained by multiple integration of the evaluated probability density function (Sc34). The control unit 10 calculates the SNE of a local network for each factor and all its neighboring factors based on a total sum of the products of the probability of the measured data and the logarithm of the probability (Sc35). The probability of the measured data is obtained from the probability density function that represents a distribution of state changes of the measured data. In other words, the computer implements the steps shown in FIG. 6.

If the calculated decrease of the SNE of a local network is beyond a predetermined criterion, the control unit 10 identifies the factor that is the center of that local network as a biomarker candidate that could be an index of a symptom of a biological object (Sc4). Step Sc4 corresponds to step s33 to step s34 in the SNE calculation process for local networks identified as step s3 in FIG. 4.

Therefore, step Sc4 involves the control unit 10 storing the factor that is the center of a local network as a DNB member into the storage unit 11 or the memory unit 12 when the value of the SNE of the local network has drastically decreased to 0 (Sc41) and storing the SNE, of the local network, whose value has decreased as a member of the "SNE group" into the storage unit 11 or the memory unit 12 (Sc42).

The control unit 10 statistically calculates, as the SNE for the entire network, a macroscopic entropy which gives a value representative of all the selected factors based on the SNEs each calculated as the microscopic entropy for a different factor (Sc5). Step Sc5 corresponds to the step identified as step s4 in FIG. 4 where the average SNE across the entire network is calculated according to Ex. (14) above.

The control unit 10 detects a pre-disease state as a precursor to a symptom change based on the factors stored in step Sc41 and the SNEs stored in step Sc42 (Sc6). Step Sc6 corresponds to the process identified as step s6 in FIG. 4 where it is determined whether or not the system is in a pre-disease state.

Therefore, step Sc6 involves the following procedures: the control unit 10 determines whether or not in the SNEs of the entire network calculated at the predetermined times in step Sc4, there exists an SNE whose value has drastically decreased; if it is determined that there exists an SNE whose value has drastically decreased, it is determined, at the time when the SNE has decreased, that the system is in a pre-disease state; on the other hand, if it is determined that there exists no SNE whose value has drastically decreased, it is determined that the system is not in a pre-disease state.

The control unit 10 then outputs results of the detection and determination from the output unit 14 before ending the process. A physician can thus determine if there is a need for a further checkup, diagnosis, consultation, treatment, or any other action based on the detection result output. The patient can learn of his/her own physical condition from the detection result output.

The embodiments above disclose only a few of numerous possible examples of the present invention and may be altered in a suitable manner in accordance with the type of disease, detection target, and other various factors. Especially, various measured data may be used as the factors provided that the measured data is information obtained by measurement on a biological object. The measured data is by no means limited to the aforementioned gene-, protein-, or metabolite-related measured data and may be, for example, various quantified conditions of body parts obtained based on images of the interior of the body obtained by a CT scanner and other measuring instruments.

REFERENCE SIGNS LIST

1 Detection device
10 Control unit
11 Storage unit
11a Detection program
11b Relationship database
12 Memory unit
13 Input unit
14 Output unit
15 Acquisition unit
16 Communications unit
16a Relationship database

The invention claimed is:

1. A detection device for detecting a pre-disease state comprising detecting a biomarker candidate that serves as an early-warning signal indicating the pre-disease state by detecting an index of a symptom of a biological object to be measured, based on measured data of a plurality of factors obtained by measurement on the biological object, said device comprising:
    selection means for selecting the factors based on time-dependent changes of measurement data of each of the factors;
    microscopic calculation means for calculating microscopic entropy as understood in statistical mechanics between the factors selected by the selection means and neighboring factors thereof;
    index detection means for detecting the index based on the microscopic entropy calculated by the microscopic calculation means;
    precursor detection means for detecting a precursor to a state transition based on the index detected by the index detection means,
    wherein the selection means selects the factors of which the measured data shows the time-dependent changes beyond a predetermined criterion,
    wherein the microscopic calculation means calculates the microscopic entropy as understood in statistical mechanics between each of the factors selected by the selection means and every neighboring factor thereof,
    wherein the precursor detection means detects the precursor to the state transition when the microscopic entropy calculated by the microscopic calculation means shows a decrease beyond a predetermined detection criterion,
    choosing means for choosing, as a candidate for a biomarker, a factor for which the microscopic entropy calculated by the microscopic calculation means shows a decrease beyond a predetermined choosing criterion, the biomarker being the index of the symptom of the biological object,
    wherein the precursor detection means detects the precursor to the state transition when the microscopic entropy for the factor chosen by the choosing means shows the decrease beyond the predetermined detection criterion; and
    an acquisition unit configured to acquire the measurement data on the plurality of factors of the biological object to be measured.

2. The detection device as set forth in claim 1, further comprising macroscopic calculation means for statistically calculating macroscopic entropy based on the microscopic entropy calculated for each of the factors by the microscopic calculation means, the macroscopic entropy being a representative value for all the selected factors,
    wherein the precursor detection means detects the precursor to the state transition when the macroscopic entropy calculated by the macroscopic calculation means shows a decrease beyond a first detection criterion and also the microscopic entropy calculated by the microscopic calculation means shows a decrease beyond a second detection criterion.

3. The detection device as set forth in claim 1, further comprising means for accessing a database that stores interactions among the factors,
    wherein the microscopic calculation means includes means for deriving a network representative of dynamical coupling among the factors based on the interactions among the factors stored in the database.

4. The detection device as set forth in claim 1, wherein the microscopic calculation means calculates, for each of the factors, the microscopic entropy based on a total sum of products of a probability of the measured data and a logarithm of the probability based on a probability density function that represents a distribution of a state change in the measured data for all the neighboring factors.

5. The detection device as set forth in claim 4, wherein the microscopic calculation means is configured to:
    binarize, for each of the factors, the measured data according to magnitude of a change relative to a threshold determined based on an earlier perturbation;
    evaluate the probability density function assuming that the binarized measured data follows a multivariate normal distribution; and
    calculate the probability of the measured data that follows a stationary distribution based on a transition probability obtained by multiple integration of the evaluated probability density function.

6. The detection device as set forth in claim 1, further comprising difference verification means for verifying whether or not the measured data for each of the factors has significantly changed with time,
    wherein the selection means selects a factor whose significance in the time-dependent change is verified.

7. The detection device as set forth in claim 1, wherein the plurality of factors include a gene-related measured item, a protein-related measured item, or a metabolite-related measured item.

8. A non-transitory computer readable medium storing a program causing a computer to execute a process for detecting an index of a symptom of a biological object to be measured, based on measured data of a plurality of factors obtained by measurement on the biological object, wherein the program causes the computer to execute:
- a selection step of selecting the factors based on time-dependent changes of measurement data of each of the factors;
- a microscopic calculation step of calculating microscopic entropy as understood in statistical mechanics between the factors selected by the selection step and neighboring factors thereof; and
- an index detection step of detecting the index based on the microscopic entropy calculated by the microscopic calculation step,
- a precursor detection step of detecting a precursor to a state transition based on the index detected by the index detection means,
- wherein the selection means selects the factors of which the measured data shows the time-dependent changes beyond a predetermined criterion,
- wherein the microscopic calculation means calculates the microscopic entropy as understood in statistical mechanics between each of the factors selected by the selection means and every neighboring factor thereof,
- wherein the precursor detection means detects the precursor to the state transition when the microscopic entropy calculated by the microscopic calculation means shows a decrease beyond a predetermined detection criterion,
- a choosing step of choosing, as a candidate for a biomarker, a factor for which the microscopic entropy calculated by the microscopic calculation means shows a decrease beyond a predetermined choosing criterion, the biomarker being the index of the symptom of the biological object,
- wherein the precursor detection means detects the precursor to the state transition when the microscopic entropy for the factor chosen by the choosing means shows the decrease beyond the predetermined detection criterion; and
- an acquisition step to acquire the measurement data on the plurality of factors of the biological object to be measured.

9. A method for detecting a pre-disease state comprising detecting a biomarker candidate that serves as an early-warning signal indicating the pre-disease state by using a detection device for detecting an index of a symptom of a biological object to be measured, based on measured data of a plurality of factors obtained by measurement on the biological object, said detection device comprising:
- selection means for selecting the factors based on time-dependent changes of measurement data of each of the factors;
- microscopic calculation means for calculating microscopic entropy as understood in statistical mechanics between the factors selected by the selection means and neighboring factors thereof;
- index detection means for detecting the index based on the microscopic entropy calculated by the microscopic calculation means;
- precursor detection means for detecting a precursor to a state transition based on the index detected by the index detection means,
- wherein the selection means selects the factors of which the measured data shows the time-dependent changes beyond a predetermined criterion,
- wherein the microscopic calculation means calculates the microscopic entropy as understood in statistical mechanics between each of the factors selected by the selection means and every neighboring factor thereof,
- wherein the precursor detection means detects the precursor to the state transition when the microscopic entropy calculated by the microscopic calculation means shows a decrease beyond a predetermined detection criterion,
- choosing means for choosing, as a candidate for a biomarker, a factor for which the microscopic entropy calculated by the microscopic calculation means shows a decrease beyond a predetermined choosing criterion, the biomarker being the index of the symptom of the biological object,
- wherein the precursor detection means detects the precursor to the state transition when the microscopic entropy for the factor chosen by the choosing means shows the decrease beyond the predetermined detection criterion; and
- an acquisition unit configured to acquire the measurement data on the plurality of factors of the biological object to be measured.

10. The method according to claim 9 further comprising:
- a selection step of selecting the factors based on time-dependent changes of measurement data of each of the factors;
- a microscopic calculation step of calculating microscopic entropy as understood in statistical mechanics between the factors selected by the selection step and neighboring factors thereof; and
- an index detection step of detecting the index based on the microscopic entropy calculated by the microscopic calculation.

* * * * *